United States Patent [19]

Höltje

[11] Patent Number: 4,544,746
[45] Date of Patent: Oct. 1, 1985

[54] PROCESS FOR PREPARING 2-ANILINOACRIDONE

[75] Inventor: Wilfried G. Höltje, Wilmington, Del.

[73] Assignee: Ciba-Geigy Corporation, Ardsley, N.Y.

[21] Appl. No.: 378,802

[22] Filed: May 17, 1982

[51] Int. Cl.$^4$ .................. C07D 219/06; C07D 219/08; C09B 48/00
[52] U.S. Cl. ..................................... 546/103; 546/49; 546/56
[58] Field of Search ............................ 546/103, 49, 56

[56] References Cited

U.S. PATENT DOCUMENTS

| | | | |
|---|---|---|---|
| 3,257,405 | 6/1966 | Gerson | 546/49 |
| 3,342,823 | 9/1967 | Dien | 546/56 X |
| 3,886,162 | 5/1975 | Pfister et al. | 546/103 |
| 4,100,162 | 7/1978 | North | 546/49 |
| 4,258,190 | 3/1981 | Taggi | 546/103 |
| 4,286,998 | 9/1981 | Höltje et al. | 106/288 Q |

FOREIGN PATENT DOCUMENTS

| | | | |
|---|---|---|---|
| 0896916 | 5/1962 | United Kingdom | 546/103 |
| 1368970 | 10/1974 | United Kingdom . | |
| 1382259 | 1/1975 | United Kingdom . | |

OTHER PUBLICATIONS

L. Kalb, Berichte 43, 2209–14, (1910).
Tai, et al., Chemical Abstracts, vol. 80, 81673y, (1974).
Brockmann, et al., Chemische Berichte, 89(6), pp. 1379, 1392, 1396–1397, (1956).
Brockmann, et al., Chemische Berichte, 89(6), pp. 1397–1402, (1956).
Fieser, et al., Reagents for Organic Synthesis, John Wiley & Sons, Inc., N.Y. (1967), pp. 156, 157, 158, 163.

Primary Examiner—Donald G. Daus
Assistant Examiner—Diana G. Rivers
Attorney, Agent, or Firm—Harry Falber

[57] ABSTRACT

A process is disclosed wherein 2,5-di(phenylamino) terephthalic acid is half-cyclized by dissolving it in a mixture of polyphosphoric acid and phosphoric acid and heating at 100°–120° C. to form 2-(phenyl)amino-3-carboxy-9(10H)acridone (ACA). The ACA is decarboxylated to form 2-(phenyl)amino-9(10H)acridone, also known as 2-anilinoacridone, by dissolving it in tetramethylene sulfone and heating in the presence of a basic cupric carbonate catalyst.

3 Claims, No Drawings

PROCESS FOR PREPARING 2-ANILINOACRIDONE

BACKGROUND OF THE INVENTION

1. Field of the Invention

This invention relates to the preparation of 2-(phenyl)amino-3-carboxy-9(10H)acridinone (ACA) and its conversion to 2-(phenyl)amino-9(10H)acridinone, also named 2-anilinoacridone (AA), by decarboxylation in tetramethylene sulfone (TMS) in the presence of basic copper carbonate catalyst. ACA is prepared by half-cyclization of 2,5-di(phenylamino)terephthalic acid (DAA) in a mixture of polyphosphoric acid (PPA) and phosphoric acid ($H_3PO_4$) at moderate temperature and short reaction time.

2. Prior Art

Quinacridonequinone has the requisites of a high-quality golden-yellow pigment except satisfactory lightfastness. This has been remedied by forming solid solutions with other components acting as stabilizers. U.S. Pat. No. 3,160,510 discloses solid solutions with quinacridone derivatives; they are limited in use by having an overall reddish color. U.S. Pat. Nos. 3,341,345 and 3,748,162 disclose colorless quinacridonequinone stabilizers such as N,N'-diphenyl-p-phenylenediamine and 6,13-dihydroquinacridone which, however, also affect the color of the final pigment composition more than is desirable.

U.S. Pat. No. 4,286,998 discloses AA and related compounds as stabilizers for quinacridonequinone pigment having minimal effect on the original quinacridonequinone color.

The compound AA was made by L. Kalb [Berichte 43, 2212 (1910)] by condensing N-phenyl-p-phenylenediamine with 2-chlorobenzoic acid in amyl alcohol and in the presence of copper powder and copper (I) chloride as catalysts to form 4'-(phenyl)amino-2-carboxydiphenylamine and cyclizing to form 2-(phenyl)amino-9(10H)acridinone. The first reaction step produces dark blue oxidation by-products which are difficult to remove from the yellow product.

British Pat. No. 1,382,259 discloses the preparation of 2(N-aryl)amino-3-carboxy-9(10H) acridinone from 2-(N-aryl)amino-3-alkoxy-carbonyl-1,4-dihydro-9(10H)acridinone which can be prepared by half-cyclizing 1,4-dialkoxy-carbonyl-2,5-di(N-aryl)amino-1,4-cyclohexadiene, as British Pat. No. 1,368,970 discloses.

U.S. Pat. No. 4,258,190 discloses the preparation of 1,2,3,4-tetrahydro-7-(phenyl)amino-9(10H)-acridinone and its dehydrogenation in the presence of supported palladium or platinum catalyst to form AA. The 1,2,3,4-tetrahydro-7-(phenyl)-amino-9(10H)acridinone can be prepared from either a 2-cyclohexanonecarboxylate ester or from the reaction product of cyclohexanone and an oxalate ester in the presence of an alkoxide base, hydrolyzed and decarbonylated to form a 2-cyclohexanonecarboxylate ester by reacting said carboxylate ester with N-phenyl-p-phenylenediamine in the presence of a catalyst to form a phenylaminocyclohexenecarboxylate ester and cyclizing to form 1,2,3,4-tetrahydro-7-(phenyl) amino-9(10H)acridinone.

SUMMARY OF THE INVENTION

The present invention relates to a novel two-step process for preparing AA from commercially available 2,5-di(phenylamino)terephthalic acid, also called 2,5-dianilino-terephthalic acid (DAA) of the formula

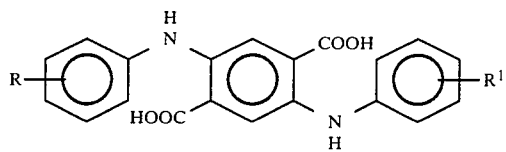

The DAA may be substituted with —R or —$R^1$ as shown in the above formula; R and $R^1$ are selected from chloro, $C_{1-4}$ alkyl and $C_{1-4}$ alkoxy. This process comprises:

(1) dissolving DAA at 40°–60° C. in a mixture of polyphosphoric acid (PPA phosphoric acid having a ratio of between 50:50 and 75:25 PPA/85% $H_3PO_4$ by volume, by mechanical stirring or, better, by a high-intensity dispersive means such as a homogenizer.

(2) heating the solution at 100°–120° C. for 5–90 minutes in a beaker or a mechanically stirred round-bottom flask fitted with a $CaSO_4$ drying tube to obtain ACA of the formula

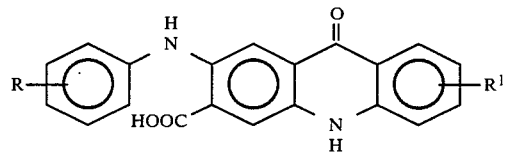

(3) separating the ACA from fully cyclized by-product quinacridone QA of the formula

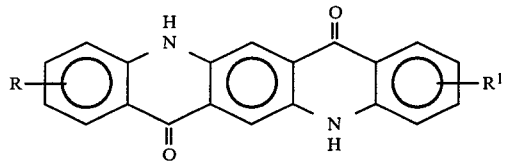

by combining the cooled reaction solution with excess water to precipitate the acid salt of ACA and by-product QA, removing phosphoric acid by washing with water, digesting the filter cake in aqueous base, such as sodium hydroxide solution at from 10° to 100° C., preferably about 60° C., for about 15 minutes, filtering while warm and washing with water, acidifying the filtrate and wash water with acetic or other acid to precipitate ACA and washing and drying it;

(4) decarboxylating the ACA in the presence of basic copper carbonate catalyst by dissolving ACA in tetramethylene sulfone at 100°–150° C. and heating it under nitrogen at 230°–260° C. for 10–60 minutes to form AA of the formula

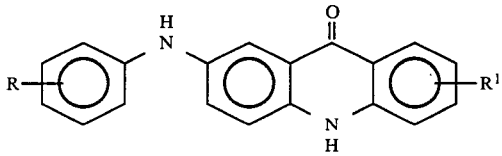

(5) isolating AA which is soluble in water-miscible tetramethylene sulfone, but insoluble in water, by filtering off the catalyst residue from the reaction solution, diluting the solution with water, filtering off the precipitated AA and washing and drying it.

DETAILED DESCRIPTION

Polyphosphoric acid in large stoichiometric excess is conventionally used as a cyclizing agent; such reactions, however, go to completion and cannot be stopped at intermediate stages. The present process permits the preparation of half-cyclized products from starting materials having two cyclizable carboxy groups of sufficiently different stepwise reactivity by carefully choosing the reaction conditions.

First the actual cyclizing agent, polyphosphoric acid, has to be diluted with phosphoric acid or the equivalent amount of water to ensure cyclization of only the first carboxy group, the second group, after half-cyclization, being less reactive. However, sufficient polyphosphoric acid has to be present to convert, if possible, all of the purple DAA starting material which is difficult to separate from the product and which when left in the product has a deleterious effect on the color of the final pigment solid solution. Separation of fully cyclized by-product, red quinacridone, is easy by comparison because ACA is soluble in bases, while quinacridone is insoluble. Any quinacridone produced is not a waste product, but can be used as pigment. In choosing the proper range of conditions between leaving unreacted starting material behind and generating by-product by overreaction it is therefore more desirable to overreact. It is most economical to convert all of the starting material and produce a minimum of fully cyclized material.

The starting material, DAA, has to be fully dissolved in the mixture of polyphosphoric and phosphoric acid to make the reaction homogeneous. A heterogeneous reaction medium leads to full cyclization.

The reaction temperature has to be low enough to prevent the onset of the second cyclization step which requires greater activation which can be provided by higher temperatures. On the other hand, the temperature has to be high enough to provide reasonable reaction rates.

Finally the reaction time has to be short enough to prevent the second cyclization step but long enough to complete the first step.

The decarboxylation of ACA by conventional, heterogeneous decarboxylation reactions with copper catalyst and quinoline or Dowtherm ® as reaction medium is generally unsatisfactory. Partial product degradation occurs, the separation of the product from the catalyst is difficult and the overall yield is relatively low. The present process avoids these problems by being quasi-homogeneous: the starting material, ACA, dissolves completely in the preferred solvent, tetramethylene sulfone (TMS), above 100° C. and below reaction temperature; the product AA stays in solution down to room temperature. After reaction, the catalyst can be easily removed from the reaction solution by filtration. The preferred solvent TMS also has the desirable property of being miscible with water; this allows easy isolation of the product, AA, by diluting the reaction solution with water, in which AA is insoluble, thereby causing precipitation of the AA. High yields are achieved.

To ensure proper dissolution of DAA before reaction onset, PPA and phosphoric acid (85%) are mixed at volume ratios of 50:50 to 75:25, respectively—preferably 67:33. The heat generated during mixing is dissipated by external cooling with water or the like until a temperature of 40°–60° C. is reached. DAA in fine powder form, predried if necessary to remove adsorbed moisture, is added to the PPA/$H_3PO_4$ blend, at ratios of 0.02 to 0.1 kg DAA/1 PPA/$H_3PO_4$, in small portions under intense mechanical stirring or under strong agitation by Gifford-Wood homogenizer or other dispersive means. Care should be taken to avoid prolonged exposure to excessive atmospheric moisture. The temperature during DAA dissolution preferably should be between 40° C. and 60° C.: high enough to speed up the dissolving process and low enough to prevent premature onset of the cyclization reaction. Dissolution can be monitored by periodically dipping a glass rod into the viscous mix and checking for solid particles clinging to the rod.

After all of the DAA is dissolved, the solution is heated to 100°–120° C. in a beaker or a mechanically stirred round-bottom flask fitted with a $CaSO_4$ drying tube, optionally under nitrogen, and kept at that temperature for between 5 and 90 minutes. The conversion of DAA to ACA can be followed by fluorescence under 366 nm UV light: DAA in PPA/$H_3PO_4$ fluoresces very weakly olive green, ACA moderately orange, fully cyclized by-product QA brightly orange-red.

The reaction solution, optionally after cooling, is poured into a 5–10 fold excess of water and stirred for 10 minutes. The maroon-colored acid salt of ACA precipitates together with by-product QA, is filtered and washed free of acid with water. To separate ACA and QA, the filter cake is digested in aqueous sodium or potassium hydroxide solution of pH 12 for 15 minutes at a temperature of 60° C. Under these conditions, ACA—being an acid—dissolves, whereas QA remains insoluble. The digestion slurry is filtered while warm and the filter cake washed with water. The filter cake of QA can be used as red/violet pigment. Filtrate and wash water are collected, combined and acidified with acid such as acetic acid or hydrochloric acid to a pH of from 4 to 1. This precipitates orange-colored ACA and—if present—unconverted purple DAA. The precipitate is filtered, washed acid-free with $H_2O$ and dried at 70°–80° C. under mild vacuum and slight $N_2$ purge.

To convert ACA to AA by decarboxylation, typically 4–10 g dry ACA, 0.5 g commercial basic cupric carbonate, $Cu(OH)_{2x}(CO_3)_{1-x}$ where X is 0.05 to 0.95 (J. T. Baker Chemical Co.), and 100 ml distilled tetramethylene sulfone (TMS) of the formula

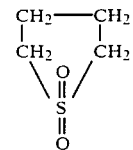

are combined in a round-bottom flask equipped with mechanical stirrer, reflux condenser and $N_2$ inlet, are heated under mechanical stirring and light $N_2$ flow to 230°–260° C. and held at that temperature for 10–60 minutes. At 100°–150° C. ACA dissolves in TMS. During the decarboxylation reaction carbon dioxide gas is evolved, in small quantities. The formed AA is soluble in TMS at all temperatures down to room temperature. The catalyst remains insoluble during and after the reaction. After completion of the reaction, the reaction slurry is cooled to 80° C. or below and filtered to remove the catalyst. The filtrate is combined with an excess of water under agitation to precipitate AA. Stirring is continued for 10 minutes. After settling, AA is filtered, washed with an excess of water to remove TMS and dried at 80° C. under vacuum and $N_2$ purge.

AA is characterized by elemental analysis (C,H,N), powder X-ray diffraction and reverse-phase high-performance liquid chromatography (HPLC). It can be recrystallized for further purification.

The product of the process of the invention, 2-(phenyl)amino-9(10H)acridinone =AA, is useful as a photostabilizer for quinacridonequinone pigments as disclosed in U.S. Pat. No. 4,286,998.

The process of the invention permits the preparation of AA as well as the preparation of its intermediate ACA.

While the commercial-grade basic copper (II) carbonate used as decarboxylation catalyst in the Examples works very well, other basic copper compounds such as copper carbonate, hydroxide, etc., as well as other copper compounds will also function as catalysts for use herein.

Other high-boiling inert solvents like Dowtherm ® A can be used as media for the decarboxylation reaction, but generally make product isolation more difficult.

EXAMPLE 1

Preparation of 2-(phenyl)amino-3-carboxy-9(10H) acridinone (ACA)

One hundred and thirty-five ml of polyphosphoric acid and 65 ml of 85% phosphoric acid are mixed in a mechanically stirred beaker and cooled to 50° C. Four grams of 2,5-di(phenylamino)terephthalic acid (DAA) are slowly added in small portions and under agitation by Gifford-Wood homogenizer. Each portion is dissolved before adding another one, checked by dipping a glass rod into the viscous reaction mixture and examining for solid particles clinging to the rod. During this time, the temperature of the reaction mixture is kept at 55° C. or below by cooling with an external water bath. After having dissolved all of the DAA, the solution is heated to 100° C. under stirring and kept at that temperature for 1 hour. The reaction mixture is cooled and poured into 2 l of water under mechanical stirring. The slurry which forms is stirred for 10 minutes and filtered. The filter cake is washed acid-free with water and the water-wet solid reslurried in 600 ml of water. The pH of the slurry is adjusted to 12 with concentrated 50% by weight aqueous NaOH solution under stirring. The slurry is heated to 60° C., held at that temperature for 10 minutes with continued stirring and filtered immediately. The filter cake is washed with water and dried in a vacuum oven at 70°–80° C. to give 0.55 g (15% yield) of quinacridone by-product. Combined filtrate and wash water are stirred and acidified with acetic acid to a pH of 4. The formed precipitate is stirred for 10 minutes, filtered and washed acid-free with water. Vacuum oven drying overnight at 70°–80° C., under slight $N_2$ purge, gives 2.8 g (74% yield) of orange microcrystalline 2-(phenyl)amino-3-carboxy-9(10H) acridinone.

EXAMPLE 2

Preparation of 2-(phenyl)amino-9(10H)acridinone (AA)

A mixture of 10 g 2-(phenyl)amino-3-carboxy-9 (10H)acridinone, 0.5 g basic cupric carbonate of the formula $Cu_2(OH)_2CO_3$ and 100 ml distilled tetramethylene sulfone is heate stirring and light $N_2$ flow, mechanical stirrer, reflux condenser and thermometer and kept at that temperature for 45 minutes. The mixture is cooled and filtered. The filtrate is combined with 100 ml of water under mechanical stirring, causing most of the AA to precipitate. The slurry is stirred for 10 minutes, left to settle, filtered and washed with 2 l of water. Drying at 80° C. overnight in a vacuum oven under light $N_2$ purge gives 8.1 g (93% yield) of yellow, microcrystalline 2-(phenyl)amino-9(10H)acridinone.

EXAMPLE 3

Preparation of 2-(phenyl)amino-3-carboxy-9(10H) acridinone (ACA)

Two hundred ml of polyphosphoric acid and 100 ml of 85% phosphoric acid are mixed in a mechanically stirred beaker and allowed to cool to 50° C. Thirty grams of 2,5-di(phenylamino)terephthalic acid (DAA) are added in small successive portions under agitation by a Gifford-Wood homogenizer, dissolving each portion before adding another one. This is checked by dipping a glass rod into the viscous reaction mixture and examining for solid particles clinging to the rod. The temperature is kept below 60° C. by external water bath cooling. After having dissolved all of the DAA, the solution is transferred into a 500 ml round-bottom flask equipped with mechanical stirrer, $CaSO_4$ drying tube and thermometer, heated to 100° C. under stirring and kept at that temperature for 30 minutes. The reaction solution is cooled to 70° C. and poured into 3 l of water under mechanical stirring. The thus formed slurry of precipitate is stirred for 10 minutes, collected by filtration, and washed acid-free with water. The water-wet solid is reslurried in 2l of water, the pH of the slurry adjusted to 12 with 50% by weight aqueous NaOH solution under stirring. The slurry is heated, kept at 60° C. for 15 minutes under continued stirring and filtered while warm. The resulting filter cake is washed with water and dried in a vacuum oven at 70°–80° C. to give 4.5 g (17% yield) of by-product quinacridone. The filtrate and wash water combined are acidified with acetic acid to a pH of 4, with stirring to precipitate ACA. The thus formed precipitate is filtered, washed acid-free with water and dried overnight at 70°–80° C. under vacuum and slight $N_2$ purge to give 21.1 g (74% yield) of orange 2-(phenyl)amino-3-carboxy-9(10H)acridinone (ACA).

EXAMPLE 4

Preparation of 2-(phenyl)amino-9(10H)acridinone (AA)

A mixture of 20 g 2-(phenyl)amino-3-carboxy-9 (10H)acridinone, 1.0 g basic cupric carbonate of the formula $Cu_2(OH)_2CO_3$ and 200 ml distilled tetramethylene sulfone is heated to 230°–235° C. in a 500 ml round-bottom flask equipped with $N_2$ inlet, mechanical stirrer, reflux condenser and thermometer, with stirring and a light $N_2$ flow, and held at that temperature for 50 minutes. The mixture is cooled and filtered. The filtrate is combined with 3 l of water under agitation, causing AA to precipitate. The slurry is stirred for 10 minutes, left to settle, filtered and washed with a large excess (3 l ) of water. Vacuum oven drying at 70°–80° C. overnight gives 15.6 g (90% yield) of 2-(phenyl)amino-9 (10H)acridinone as yellow microcrystalline powder.

EXAMPLE 5

Preparation of 2-(p-tolyl)amino-3-carboxy-7-methyl-9 (10H)acridinone (TMCA)

Two hundred ml of polyphosphoric acid and 100 ml of 85% phosphoric acid are mixed in a mechanically stirred beaker and allowed to cool to 40° C. Thirty grams of 2,5-di(p-tolylamino)terephthalic acid (DTTA) are added in small portions, successively, under intense agitation by Gifford-Wood homogenizer. Care is taken to dissolve each portion before adding another one. The temperature is kept below 60° C. by external water bath cooling. After having dissolved all of the DTTA, as ascertained by dipping a glass rod into the viscous reaction medium and examining for solid particles clinging to the rod, the solution is transferred into a 500 ml round-bottom flask equipped with mechanical stirrer, $CaSO_4$ drying tube, $N_2$ inlet and thermometer, and heated to 100° C. within 45 minutes with stirring. The temperature is held at 100° C. for 45 minutes. The solution develops an orange-brown fluorescense during this time. The solution is poured into 2 l of water with mechanical stirring, generating a dark-colored precipitate. Stirring is continued for 10 minutes. The precipitate is filtered, washed acid-free with water and suspended in 2 l of $H_2O$. The suspension is made basic with a pH of 12 by adding 50 wt % aqueous NaOH solution with stirring, is heated, kept at 60° C. for 15 minutes with continued stirring and filtered while warm. The filter cake is washed with water and dried in a vacuum oven at 70°-80° C. to give 4.0 g (15% yield) of apparently 2,9-dimethylquinacridone by-product. The filtrate and wash water combined are acidified with acetic acid to a pH of 4, with stirring. The resulting red precipitate is filtered, washed acid-free with water and dried overnight at 70°-80° C. under vacuum and slight $N_2$ purge to give 22.3 g (78% yield) of red 2-(p-tolyl)amino-3-carboxy-7-methyl-9(10H)acridinone (TMCA).

EXAMPLE 6

Preparation of 2-(p-tolyl)amino-7-methyl-9(10H)acridinone (TMA) by decarboxylation A mixture of 20 g 2-(p-tolyl)amino-3-carboxy-7-methyl-9(10H) acridinone, as prepared in example 5, 2.0 g basic cupric carbonate of the formula $Cu_2(OH)_2CO_3$ and 200 ml distilled tetramethylene sulfone is heated to 230° C. in a 500 ml round-bottom flask equipped with $N_2$ inlet, mechanical stirrer, reflux condenser and thermometer with stirring and light $N_2$ flow, and held at that temperature for 45 minutes. The mixture is cooled, left overnight and filtered the next day. The filtrate is combined with 1 l of water with agitation, causing TMA to precipitate. The suspension is stirred for 10 minutes and left to settle. It is filtered, washed with a large excess of water and dried overnight at 75° C. in a vacuum oven with slight $N_2$ purge to give 4.0 g of yellow 2-(p-tolyl)amino-7-methyl-9(10H) acridinone (TMA) microcrystalline pwoder. In this case, the catalyst filter cake still contains large amounts of TMA, apparently due to lower room-temperature solubility of TMA in tetramethylene sulfone and greater probability of crystallization on overnight standing.

The catalyst filter cake, therefore, is slurried in 250 ml acetone in an Erlenmeyer flask, heated to 50° C., digested at that temperature for 5 minutes, with magnetic stirring and filtered warm. The filtrate is poured into 1l of water with stirring and the resulting suspension stirred for 10 minutes and filtered. The filter cake is washed with water and vacuum dried at 75° C. with slight $N_2$ purge to give additional 0.7 g of yellow TMA.

To extract the remaining TMA from the catalyst filter cake, the filter cake is heated with 250 ml dimethyl sulfoxide, a more powerful solvent, in an Erlenmeyer flask at 60°-80° C. under magnetic stirring for 5 minutes and filtered hot. The filtrate is poured into 2 l of water, the resulting suspension stirred for 10 minutes and filtered. The filter cake is washed with excess water and dried at 75° C. in a vacuum oven with slight $N_2$ purge to give 6.7 g of yellow TMA microcrystalline powder for a total yield of 65%.

I claim:

1. A process comprising dissolving at from about 40° C. to about 60° C. a compound of the formula

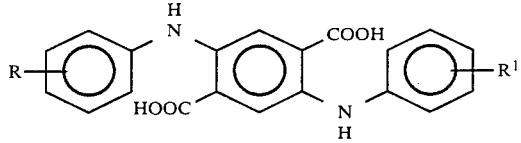

wherein R and $R^1$ are —H, —Cl, $C_{1-4}$ alkyl or $C_{1-4}$ alkoxy, in a mixture of 50 to 75 volume percent polyphosphoric acid and 50 to 25 volume percent phosphoric acid, calculated as 85% aqueous phosphoric acid, heating the solution to 100° to 120° C. for 5 to 90 minutes and recovering a compound of the formula

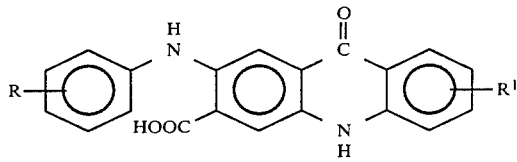

2. The process of claim 1 wherein the reaction solution is cooled, diluted with water and filtered, the resulting filter cake digested in aqueous base at 10° C. to 100° C. and filtered to remove any

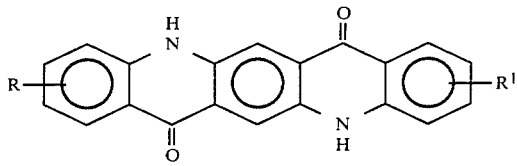

which may have formed.

3. The process of claim 2 wherein the filtrate remaining after removal of

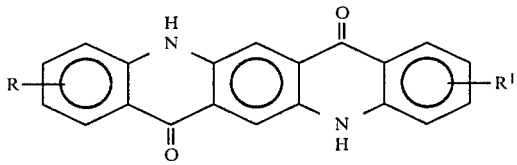

is acidified to precipitate

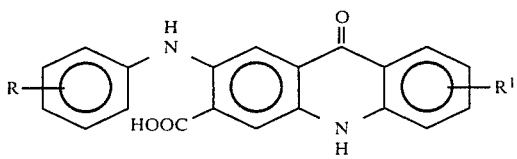

* * * * *